US00PP32254P2

(12) United States Plant Patent
Koot

(10) Patent No.: US PP32,254 P2
(45) Date of Patent: Sep. 29, 2020

(54) ***CALIBRACHOA* PLANT NAMED 'DOCALALNATROPIC'**

(50) Latin Name: ***Calibrachoa* X *hybrida***
Varietal Denomination: Docalalnatropic

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,355

(22) Filed: Sep. 23, 2019

(51) Int. Cl.
*A01H 6/82* (2018.01)
*A01H 5/02* (2018.01)

(52) U.S. Cl.
USPC ..... Plt./413

(58) Field of Classification Search
USPC ..... Plt./413
CPC ..... A01H 6/82; A01H 5/02
See application file for complete search history.

(56) References Cited

PUBLICATIONS

PLUTO Plant Variety Database Apr. 2, 2020. p. 1.*

* cited by examiner

*Primary Examiner* — Annette H Para
(74) *Attorney, Agent, or Firm* — C. A. Whealy

(57) ABSTRACT

A new and distinct cultivar of *Calibrachoa* plant named 'Docalalnatropic', characterized by its semi-upright to outwardly spreading, trailing and decumbent plant habit; vigorous growth habit; freely branching habit; early and freely flowering habit; large flowers with yellow-colored petals with random red purple-colored speckles; and good garden performance.

2 Drawing Sheets

Figure 1:
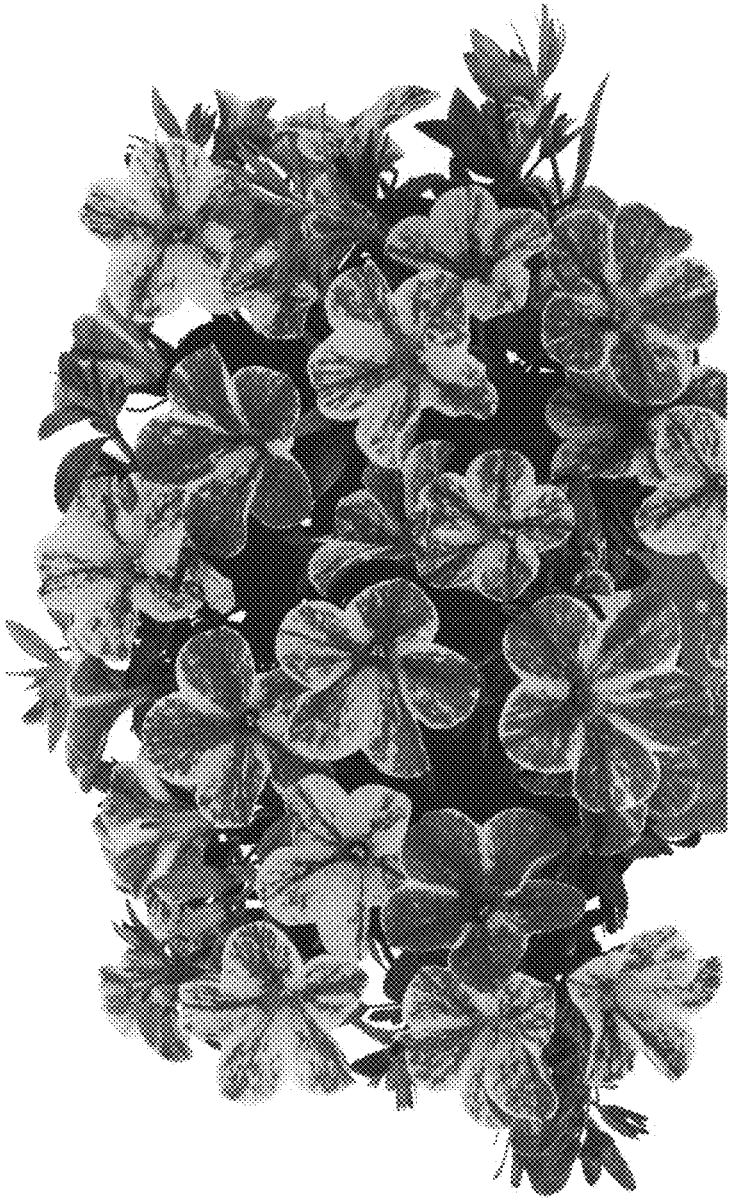

Botanical designation: *Calibrachoa* X *hybrida.*
Cultivar denomination: 'DOCALALNATROPIC'.

BACKGROUND OF THE INVENTION

The present invention relates to a new and distinct cultivar of *Calibrachoa* plant, botanically known as *Calibrachoa* X *hybrida* and hereinafter referred to by the name 'Docalalnatropic'.

The new *Calibrachoa* plant is a naturally-occurring whole plant mutation of a proprietary selection of *Calibrachoa* X *hybrida* identified as code number AA14-002732-006, not patented. The new *Calibrachoa* plant was discovered and selected by the Inventor as a single flowering plant from within a population of plants of the mutation parent selection in a controlled greenhouse environment in Rheinberg, Germany in May, 2018.

Asexual reproduction of the new *Calibrachoa* plant by vegetative terminal cuttings in a controlled greenhouse environment in Rheinberg, Germany since June, 2018 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Docalalnatropic'. These characteristics in combination distinguish 'Docalalnatropic' as a new and distinct *Calibrachoa* plant:

1. Semi-upright to outwardly spreading, trailing and decumbent plant habit.
2. Vigorous growth habit.
3. Freely branching habit.
4. Early and freely flowering habit.
5. Large flowers with yellow-colored petals with random red purple-colored speckles.
6. Good garden performance.

The new *Calibrachoa* can be compared to plants of the mutation parent selection. Plants of the new *Calibrachoa* differ primarily from plants of the mutation parent selection in the flower color as plants of the mutation parent selection have red-colored flowers.

Plants of the new *Calibrachoa* can be compared to plants of *Calibrachoa* sp. 'Docalalnarec', not patented. In side-by-side comparisons, plants of the new *Calibrachoa* differ primarily from plants of 'Docalalnarec' in the following characteristics:

1. Plants of the new *Calibrachoa* have slightly larger flowers than plants of 'Docalalnarec'.
2. Plants of the new *Calibrachoa* and 'Docalalnarec' differ in flower color as plants of 'Docalalnatropic' have yellow-colored petals with random red purple-colored speckles whereas plants of 'Docalalnarec' have red purple-colored flowers with yellow-colored centers.
3. Plants of the new *Calibrachoa* have narrower sepals than plants of 'Docalalnarec'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet (FIG. 1 of 2) is a side perspective view of a typical flowering plant of 'Docalalnatropic' grown in a container.

Figure 2:
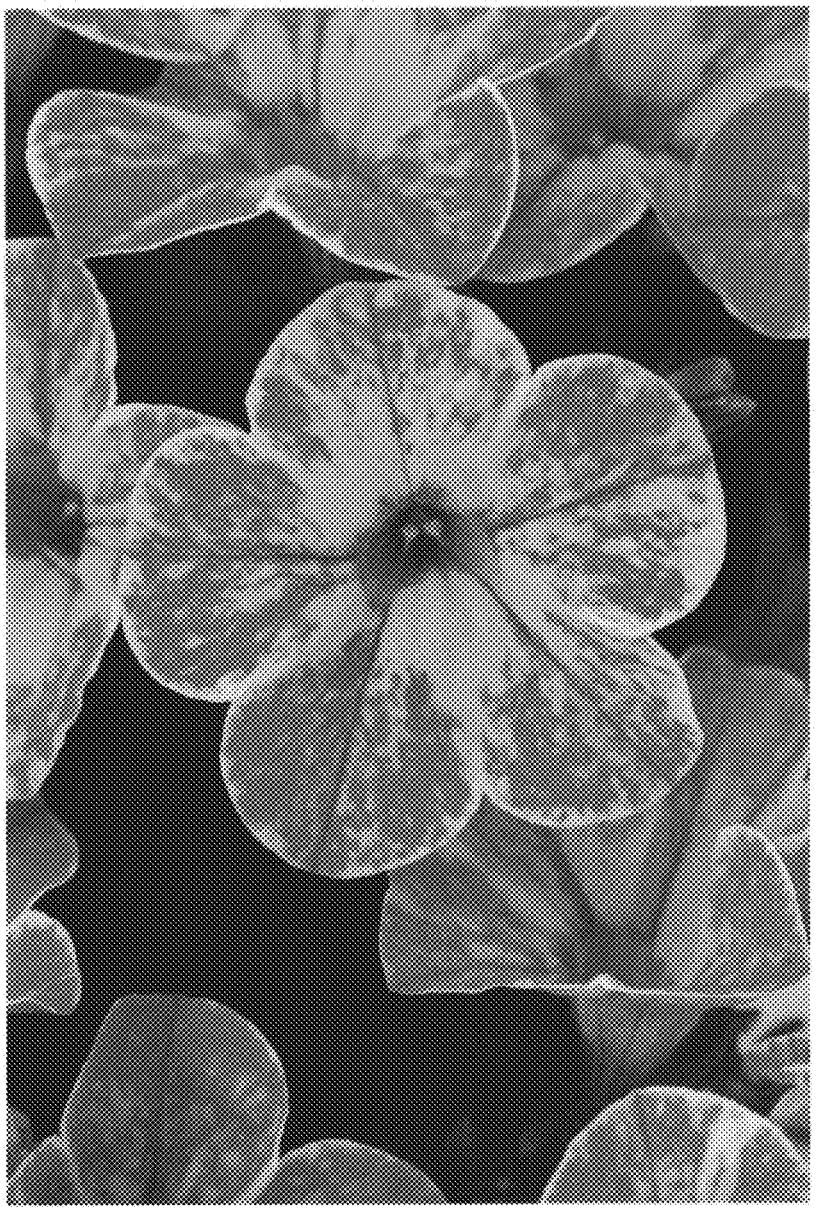

The photograph on the second sheet (FIG. 2 of 2) is a close-up view of typical flowers of 'Docalalnatropic'.

DETAILED BOTANICAL DESCRIPTION

The aforementioned photographs and following observations, measurements and values describe plants grown during the spring in 13-cm containers in a glass-covered greenhouse in Rheinberg, Germany and under cultural practices typical of commercial *Calibrachoa* production. During the production of the plants, day and night temperatures averaged 18° C. and light levels averaged 1,500 lux. Rooted young plants were pinched one time three weeks after planting and were twelve weeks old when the photographs and description were taken. In the following description, color references are made to The Royal Horticultural Society Colour Chart, Fifth Edition, except where general terms of ordinary dictionary significance are used.

Botanical classification: *Calibrachoa* X *hybrida* 'Docalalnatropic'.

Parentage: Naturally-occurring whole plant mutation of a proprietary selection of *Calibrachoa* X *hybrida* identified as code number AA14-002732-006, not patented.

Propagation:

- *Type*.—By vegetative cuttings.
- *Time to initiate roots, summer*.—About five days at temperatures about 20° C.
- *Time to initiate roots, winter*.—About seven days at temperatures about 20° C.
- *Time to produce a rooted young plant, summer*.—About three weeks at temperatures about 20° C.
- *Time to produce a rooted young plant, winter*.—About four weeks at temperatures about 20° C.
- *Root description*.—Fine, fibrous; close to 158A in color, actual color of the roots is dependent on substrate composition, water quality, fertilizers, substrate temperature and age of roots.
- *Rooting habit*.—Freely branching; dense.

Plant description:

- *Plant and growth habit*.—Semi-upright to outwardly spreading to trailing and decumbent plant habit; freely branching habit with about eight to ten primary lateral branches each with about eleven secondary lateral branches developing per plant; pinching enhances branching; dense and full appearance; vigorous growth habit; moderate growth rate.
- *Plant height, soil level to top of foliar plane*.—About 14.5 cm.
- *Plant height, soil level to top of floral plane*.—About 14.5 cm.
- *Plant diameter* (*spread of plant*).—About 45 cm.

Lateral branch description:

- *Length*.—About 24 cm.
- *Diameter*.—About 3 mm.
- *Internode length*.—About 2 cm.
- *Strength*.—Strong.
- *Aspect*.—Initially upright to outwardly spreading to trailing and decumbent.
- *Texture and luster*.—Pubescent; glossy.
- *Color, developing and developed*.—Close to 144A to 144B.

Leaf description:

- *Arrangement*.—Before flowering, alternate, and after flowering, opposite; simple.
- *Length*.—About 3 cm.
- *Width*.—About 1.2 cm.
- *Shape*.—Oblanceolate.
- *Apex*.—Rounded.
- *Base*.—Attenuate.
- *Margin*.—Entire.
- *Texture and luster, upper and lower surfaces*.—Pubescent; matte.
- *Venation pattern*.—Pinnate; arcuate.
- *Color*.—Developing leaves, upper surface: Close to 137B to 137C. Developing leaves, lower surface: Close to 138B. Fully expanded leaves, upper surface: Close to 137B; venation, close to 144C. Fully expanded leaves, lower surface: Close to 137C; venation, close to 144B.
- *Petioles*.—Length: About 3 mm. Diameter: About 2 mm. Strength: Moderately strong. Texture and luster, upper and lower surfaces: Pubescent; matte. Color, upper surface: Close to 144B. Color, lower surface: Close to 144C.

Flower description:

- *Flower arrangement and habit*.—Single salverform flowers arising from leaf axils; freely flowering habit with usually about 40 flowers and about 15 flower buds per plant during the flowering season; flowers face upright to outwardly.
- *Fragrance*.—None detected.
- *Natural flowering season*.—Early flowering habit, plants of the new *Calibrachoa* initiate and develop flowers about six weeks after planting; plants flower continuously from the spring throughout the summer in Germany.
- *Flower longevity*.—Individual flowers last about seven to ten days on the plant; flowers not persistent.
- *Flower buds*.—Length: About 2 cm. Diameter: About 4 mm. Shape: Elongated oblong. Texture and luster: Rippled, pubescent; semi-glossy. Color: Close to 2B and N78A.
- *Flower diameter*.—About 3.5 cm.
- *Flower depth* (*height*).—About 2.8 cm.
- *Flower throat diameter*.—About 8 mm.
- *Flower tube length*.—About 1.5 cm.
- *Flower tube diameter*.—About 2.5 mm.
- *Corolla*.—Arrangement: Five petals fused at the base and opening into a flared trumpet. Petal length from throat: About 1.7 cm. Petal lobe width: About 1.6 cm. Petal shape: Roughly spatulate. Petal apex: Rounded. Petal margin: Entire; slightly undulate. Petal texture and luster, upper and lower surfaces: Smooth, glabrous; matte. Throat texture: Smooth, glabrous. Tube texture: Smooth, glabrous. Color: Petal, when opening, upper surface: Ground color, close to 12A; random speckles, close to 66B. Petal, when opening, lower surface: Ground color, close to 12C; random speckles, close to 67B. Petal, fully opened, upper surface: Ground color, close to 12A; random speckles, close to 66A; venation, close to 46A; with development, ground color becoming closer to 6A and random speckles, closer to 72C. Petal, fully opened, lower surface: Ground color, close to 12C; random speckles, close to 67B; venation, close to 166A; with development, ground color becoming closer to 6A and random speckles, closer to 72C. Throat: Close to 7A; venation, close to 72A. Tube: Close to 3C; venation, close to 200C.

*Calyx*.—Arrangement: Star-shaped calyx with five sepals; sepals fused at the base. Sepal length: About 1.6 cm. Sepal width: About 1 cm. Sepal shape: Lanceolate. Sepal apex: Acute. Sepal margin: Entire. Sepal texture and luster, upper and lower surfaces: Pubescent; matte. Color: When developing and fully developed, upper surface: Close to 143A. When developing and fully developed, lower surface: Close to 143B.

*Peduncles*.—Length: About 5 cm. Diameter: About 2 mm. Angle: About 45° from stem axis. Strength: Moderately strong. Texture and luster: Pubescent; matte. Color: Close to 144B.

*Reproductive organs*.—Stamens: Quantity: Five per flower. Filament length: About 9 mm. Filament color: Close to 2C. Anther length: About 1 mm. Anther shape: Ellipsoidal. Anther color: Close to 13A. Pollen amount: Scarce. Pollen color: Close to 10C. Pistils: Quantity: One per flower. Pistil length: About 1.1 cm. Style length: About 7 mm. Style color: Close to 149B. Stigma diameter: About 1 mm. Stigma shape: Ellipsoidal. Stigma color: Close to 149B. Ovary color: Close to 149B. Fruits: Quantity produced per plant: About ten during the flowering season. Length: About 6 mm. Diameter: About 4 mm. Texture: Smooth, glabrous. Color: Close to N199C. Seeds: Quantity per flower: About 55. Length: About 1 mm. Diameter: About 1 mm. Texture: Smooth, glabrous. Color: Close to 200A.

Garden performance: Plants of the new *Calibrachoa* have been observed to have good garden performance and to tolerate wind, rain, temperatures ranging from about 3° C. to about 28° C. and to be suitable for USDA Hardiness Zone 11.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'Docalalnatropic' as illustrated and described.

* * * * *